(12) United States Patent
Martins et al.

(10) Patent No.: US 11,364,012 B2
(45) Date of Patent: Jun. 21, 2022

(54) 3-D IMAGING VIA FREE-HAND SCANNING WITH A MULTIPLANE US TRANSDUCER

(71) Applicant: B-K Medical Aps, Herlev (DK)

(72) Inventors: Bo Martins, Rodovre (DK); Fredrik Gran, Limhamn (SE); Svetoslav Nikolov, Farum (DK)

(73) Assignee: BK Medical APS, Herlev (DK)

( * ) Notice: Subject to any disclaimer, the term of this patent is extended or adjusted under 35 U.S.C. 154(b) by 1422 days.

(21) Appl. No.: 15/609,807

(22) Filed: May 31, 2017

(65) Prior Publication Data

US 2018/0344291 A1 Dec. 6, 2018

(51) Int. Cl.
*A61B 8/08* (2006.01)
*A61B 8/12* (2006.01)
*A61B 10/02* (2006.01)
*A61B 8/00* (2006.01)
*A61B 10/04* (2006.01)

(52) U.S. Cl.
CPC .............. *A61B 8/483* (2013.01); *A61B 8/085* (2013.01); *A61B 8/12* (2013.01); *A61B 8/445* (2013.01); *A61B 8/5207* (2013.01); *A61B 8/5253* (2013.01); *A61B 10/0241* (2013.01); *A61B 8/4466* (2013.01); *A61B 8/485* (2013.01); *A61B 10/04* (2013.01); *A61B 2010/045* (2013.01)

(58) Field of Classification Search
None
See application file for complete search history.

(56) References Cited

U.S. PATENT DOCUMENTS

| 6,171,248 B1 * | 1/2001 | Hossack ................. A61B 8/12 600/447 |
| 6,306,091 B1 * | 10/2001 | Sumanaweera ..... G01S 7/52023 128/916 |
| 9,259,208 B2 | 2/2016 | Nygaard et al. |

(Continued)

OTHER PUBLICATIONS

Evangelidis et al., Parametric Image Alignment Using Enhanced Correlation Coefficient Maximation, IEEE Trans.on Pattern Analysis and Machine Intelligence, vol. 30, No. 10, Oct. 2008.

(Continued)

*Primary Examiner* — Shahdeep Mohammed
(74) *Attorney, Agent, or Firm* — Daugherty & Del Zoppo, Co. LPA (57) ABSTRACT

An ultrasound imaging system includes a biplane ultrasound probe and a console. The biplane ultrasound probe includes a sagittal array and a transverse array. The console includes a transmit circuit, a receive circuit, and an image generator. The transmit circuit is configured to control the sagittal and transverse arrays to emit ultrasound signals while the probe is manually rotated and translated. The receive circuit is configured to receive electrical signal produced by the sagittal and transverse arrays in response to the sagittal and transverse arrays receiving echoes produced in response to the corresponding ultrasound signals interreacting with structure. The image generator is configured to construct a three-dimensional image with the electrical signals from the sagittal or transverse array using the electrical signals from both the sagittal and transverse arrays to track the motion of the probe and align scanplanes.

21 Claims, 3 Drawing Sheets

(56) References Cited

U.S. PATENT DOCUMENTS

| | | | | |
|---|---|---|---|---|
| 2007/0232892 | A1* | 10/2007 | Hirota | A61B 5/0066 |
| | | | | 600/407 |
| 2012/0004552 | A1* | 1/2012 | Kamiyama | G01S 7/5205 |
| | | | | 600/443 |
| 2012/0287311 | A1* | 11/2012 | Chuang | H04N 5/2628 |
| | | | | 348/240.2 |
| 2013/0137979 | A1* | 5/2013 | Deckman | A61B 18/1485 |
| | | | | 600/439 |
| 2015/0133784 | A1* | 5/2015 | Kapoor | A61B 8/4254 |
| | | | | 600/438 |
| 2015/0363429 | A1* | 12/2015 | Doi | G16H 50/70 |
| | | | | 382/133 |
| 2016/0328998 | A1* | 11/2016 | Pedersen | A61B 8/4254 |

OTHER PUBLICATIONS

Nikolov, et al., 3D synthetic aperture imaging using a virtual source element in the elevation plane, IEEE Int'l. US Symposium, Puerto Rico, 2000.

Nikolov, et al., Synthetic aperture imaging using a semi-analytic model for the transit beams, IEEE Int'l. US Symposium, Taiwan, Oct. 2015.

* cited by examiner

3-D IMAGING VIA FREE-HAND SCANNING WITH A MULTIPLANE US TRANSDUCER

TECHNICAL FIELD

The following generally relates to ultrasound and more particularly to three-dimensional (3-D) ultrasound imaging via free-hand scanning with a multiplane ultrasound (US) transducer.

BACKGROUND

An ultrasound imaging system has included an ultrasound probe with a transducer array and a console. The ultrasound probe houses the transducer array, and the console includes a display monitor and a user interface. The transducer array transmits an ultrasound signal and receives echoes produced in response to the signal interacting with structure. The echoes are converted to electrical signals by the transducer array and are conveyed to the console. The console processes the electrical signals, producing an image.

For three-dimensional (3-D) imaging, various approaches have been employed. For example, one approach is to use a probe with a mover that rotates the probe or transducer array where data is acquired during the movement to acquire volumetric data. Unfortunately, external movers attached to the outside of the probe are in the way of external needle guides e.g., for biopsy needles, and internal movers occupy space inside a probe preventing the passing of a biopsy needle therethrough and external guides shadow the field of view.

Another approach is to use a two-dimensional (2-D) transducer array. A 2-D array, relative to a one-dimensional (1-D) array, includes more transducer elements and thus more interconnects and channels. Unfortunately, this adds cost, weight, and complexity, and requires a larger cable between the probe and the console with more wires. Another approach is to use a transducer with two one-dimensional arrays in a fixed geometrical structure and visually presenting the images from the different arrays where the clinician mentally reconstructs a 3-D volume form the 2-D planes. Unfortunately, the manner in which the planes intersect is not intuitive.

SUMMARY

Aspects of the application address the above matters, and others.

In one aspect, an ultrasound imaging system includes a biplane ultrasound probe and a console. The biplane ultrasound probe includes a sagittal array and a transverse array. The console includes a transmit circuit, a receive circuit, and an image generator. The transmit circuit is configured to control the sagittal and transverse arrays to emit ultrasound signals while the probe is manually rotated and translated. The receive circuit is configured to receive electrical signals produced by the sagittal and transverse arrays in response to the sagittal and transverse arrays receiving echoes produced in response to the corresponding ultrasound signals interreacting with structure. The image generator is configured to construct a three-dimensional image with the electrical signals from the sagittal or transverse array using the electrical signals from both the sagittal and transverse arrays to track the motion of the probe and align scanplanes.

In another aspect, a method includes employing a biplane transducer probe of a first imaging modality to acquire data in both sagittal and transverse planes while the probe is manually translated. The method further includes tracking rotational motion of the probe with data for the transverse planes. The method further includes tracking translational motion of the probe with data for the sagittal planes. The method further includes generating volume data with the data for the sagittal or transverse planes using the tracked rotational and translational motions to align the data in the volume.

In another aspect, a console of an ultrasound imaging system includes a transmit circuit, a receive circuit, and an image generator. The transmit circuit is configured to control sagittal and transverse arrays of a biplane probe to emit ultrasound signals while the probe is manually rotated and translated. The receive circuit is configured to receive electrical signal produced by the sagittal and transverse arrays in response to the sagittal and transverse arrays receiving echoes produced in response to the corresponding ultrasound signals interreacting with structure. The image generator is configured to construct a three-dimensional image with the electrical signals from the sagittal or transverse array using the electrical signals from both the sagittal and transverse arrays to track the motion of the probe and align scanplanes.

Those skilled in the art will recognize still other aspects of the present application upon reading and understanding the attached description.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 1:
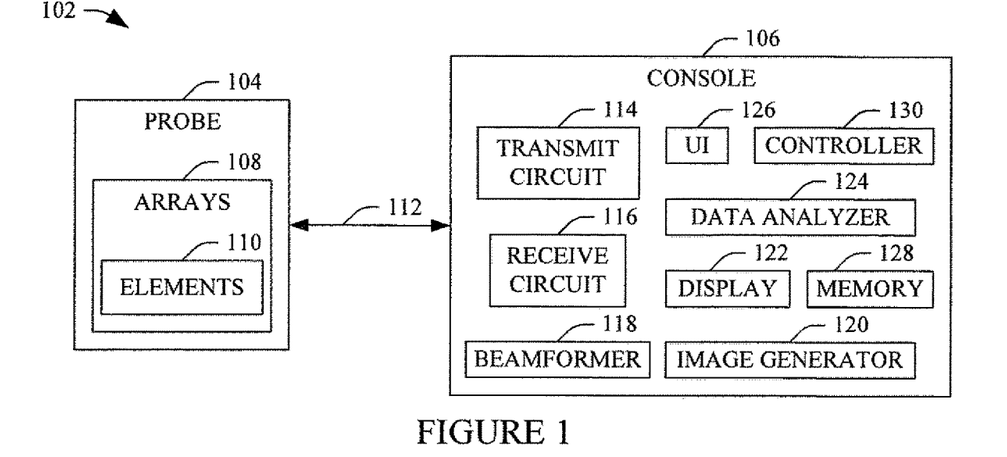
FIG. 1 schematically illustrates an example ultrasound imaging system with a probe including a biplane transducer array.

FIG. 1 schematically illustrates an imaging system 102, such as ultrasound imaging system, including an ultrasound probe 104 and a console 106.

The probe 104 includes at least two transducer arrays 108, each array including a plurality of transducer elements 110. The at least two transducer arrays 108 are spatially arranged in the probe 104 transverse to each other. For example, in one embodiment the probe 104 is a biplane probe with two transducer arrays, a sagittal array and a transverse (axial) array, which are spatially arranged transverse to each other where their fields of view cross. Each of the transducer arrays 108 can be a 1-D, 2-D etc. array. Examples of 1-D arrays include 16, 64, 128, 196, 256, etc. element arrays. 2-D arrays can be square, rectangular, circular, etc.

The transducer arrays 108 are configured to generate pressure waves in response to excitation signals. The transducer arrays 108 are further configured to receive echo signals, which are produced in response to an interaction of the pressure waves with structure such as anatomical tissue, organs, cells, etc., and produce electrical (RF) signals indicative of the received echo signals. The electrical signals are transferred to the console 106 via a communication path 112, which can include a hardware channel (e.g., a cable) and/or a wireless channel.

For some procedures, the probe 104 is manually rotated by hand (free hand) during scanning and acquires data at a plurality of angularly offset field of views. The probe 104 may also be translated (e.g., pushed and/or pulled), e.g., intentionally e.g., to scan a larger object. The probe 104 may also be unintentionally translated through unintentional hand movement. An example of such a procedure is prostate imaging. For this, the probe 104 is an endocavitary probe and ultrasound examination is performed transrectally. The probe is first positioned close to the prostate, and then data is acquired with the at least one array 108 while the user rotates (and/or translates) the probe 104 over an arc.

The console 106 includes a transmit circuit 114 and a receive circuit 116. The transmit circuit 114 transmits a control signal(s), via the communication path 112 and to the probe 104, that excites one or more of the transducer element(s) 110 of the transducer arrays 108, which causes the transducer element(s) 110 to transmit the pressure wave. The receive circuit 116 receives, via the communication path 112 and from the probe 104, the electrical signals produced by the element(s) 110 of the transducer array 108.

The console 106 further includes a beamformer 118 configured to process the received electrical signals. In one instance, this includes beamforming individual sagittal and transverse scanplanes, plane-by-plane, from the electrical signals. In another instance, the beamformer 118 employs a synthetic aperture algorithm to compute data points for a volume from the electrical signals. Other processing may lower speckle, improve specular reflector delineation, and/or includes FIR filtering, IIR filtering, etc. The electrical signals can first be amplified and/or otherwise pre-processed and/or conditioned.

The console 106 further includes an image generator 120. The image generator 120 is configured to process individual sagittal and transverse scanplanes and/or the data points for the volume and generates a 3-D image. As described in greater detail below, in one instance the image generator 120 uses the data from both the sagittal and transverse scanplanes as alignment/tracking planes to estimate translational and rotation movement of the probe 104 which is used to translationally and/or rotationally align the sagittal scanplanes and/or the data points to generates the 3-D image. In one instance, this can mitigate unintentional free-hand translational movement of the probe 104 during scanning and/or provides a measurement accurate 3-D reconstruction.

The console 106 further includes a display 122 configured to display individual image scanplanes and/or the 3-D image. The console 106 further includes a data analyzer 124. The data analyzer 124 is configured to analyze the scanplanes. This includes estimating the above noted translational and rotation movement from the sagittal and transverse scanplanes. This also includes determining whether the probe 104 is being rotated too fast or too slow from the transverse scanplanes. The results of the analysis can be visually presented via the display 122 through text, numbers, color, graphical indicia, a combination thereof, and/or otherwise, e.g., through an audible and/or haptic signal.

The console 106 further includes a user interface (UI) 126, which includes at least one or more input devices (e.g., a button, a touchscreen, etc.), which allows for interaction with the system 102. Such interaction may include segmenting, rotating, panning, zooming, and/or otherwise manipulating displayed data. The console 106 further includes a memory device ("memory") 128 that can be used to store the electrical signals, the sagittal and transverse scanplanes, the 3-D image, etc. The console 106 further includes a controller 130 configured to control one or more components of the console 106.

Figure 2:
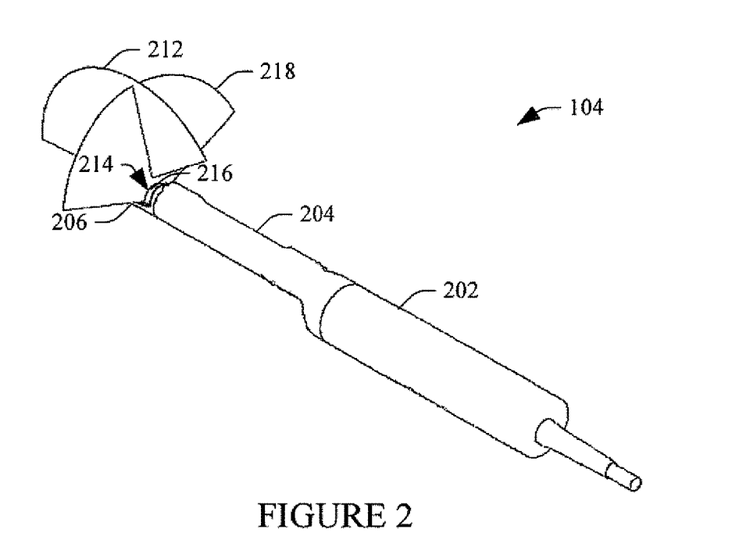
FIG. 2 schematically illustrates a perspective view of an example of the probe.
Figure 3:
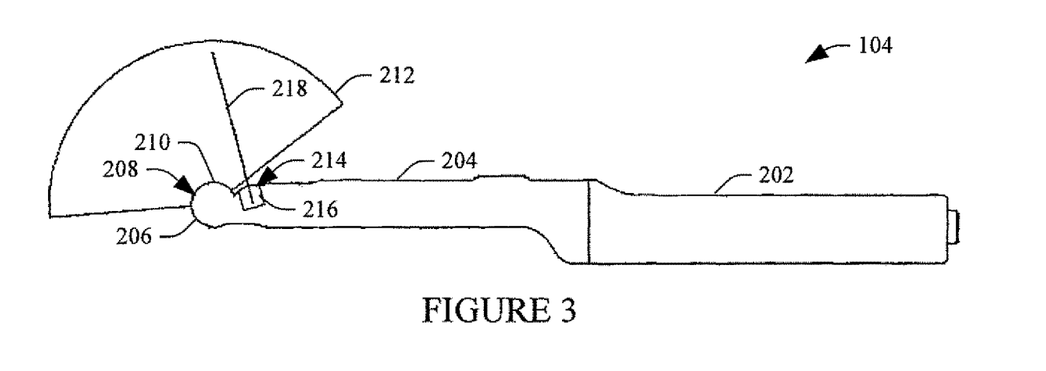
FIG. 3 schematically illustrates a side view of the example probe.

FIGS. 2 and 3 schematically illustrate a non-limiting embodiment of the probe 104 configure as a biplane transducer. FIG. 2 shows a perspective view of the probe 104, and FIG. 3 shows a side view of the probe 104.

In FIGS. 2 and 3, the probe 104 includes a handle 202, a shaft 204, a head 206, a sagittal array 208 (of the arrays 108) behind a first acoustic window 210 and configured to provide a sagittal field of view (FOV) 212, and a transverse array 214 (of the arrays 108) behind a second acoustic window 216 and configured to provide a transverse FOV 218. Another example of a suitable biplane probe 104 is described in U.S. Pat. No. 9,259,208 B1, filed Oct. 20, 2009, and entitled "Ultrasound Probe," which is incorporated herein by reference in its entirety. Other suitable probes include but are not limited to the I12C5b, E14C4t, E10C4 and/or E14CL4b probes, products of B-K Medical ApS, Herlev, DK. Although the illustrated arrays 208 and 214 are perpendicular to each other, it is to be understood that the arrays 208 and 214 do not have to be perpendicular to each other.

FIGS. 4-7 illustrate example data acquisition using freehand motion and generation of a 3-D image from the acquired data.

Figure 4:
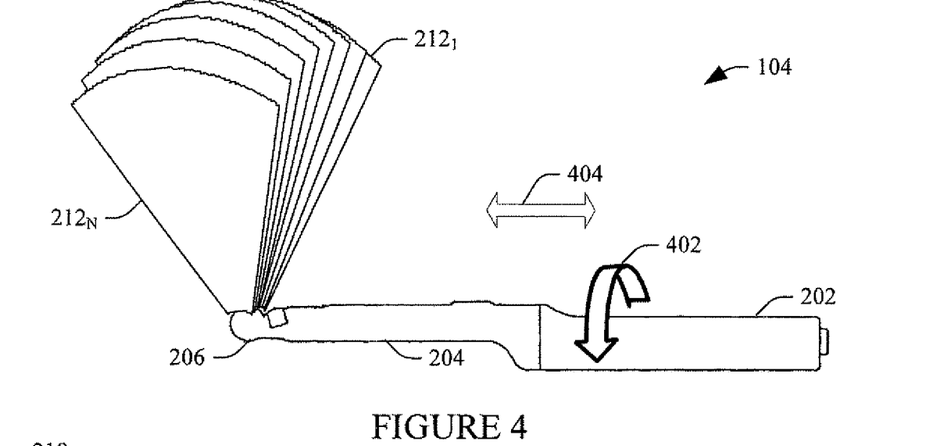
FIG. 4 schematically illustrates the example probe rotating and translating and field of views only of the sagittal array.

FIG. 4 shows acquisition where an operator rotates the probe 104 through an arc 402. Data for a number of sagittal FOVs $212_1, \ldots, 212_N$, where N is a positive integer, is acquired while the probe 104 rotates. The corresponding transverse FOVs 218 are not shown in FIG. 4, e.g., so as not to visually obscure the sagittal FOVs $212_1, \ldots, 212_N$. However, it is clear from the description herein that the transverse FOVs 218 rotate therewith. FIG. 4 also shows intentional and/or unintentional translational motion 404.

Figure 5:
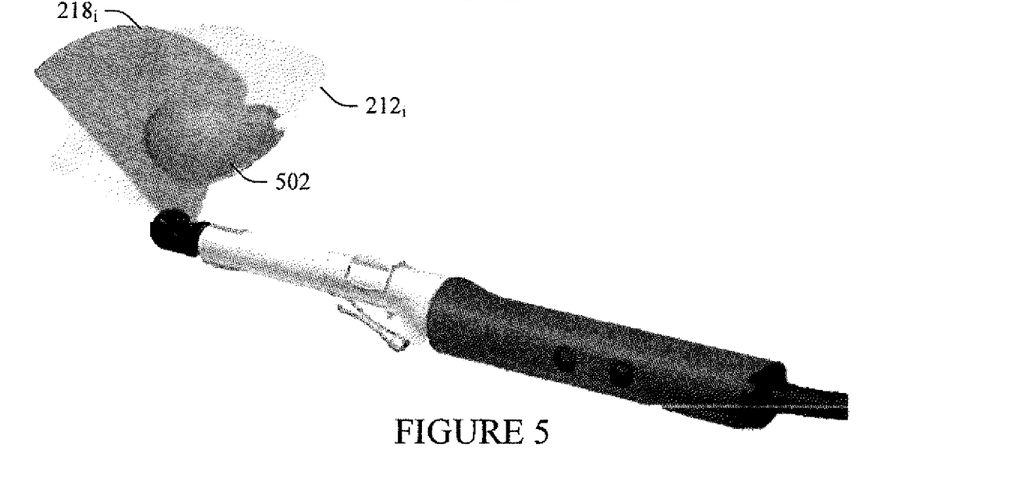
FIG. 5 illustrates a sagittal and a transverse field of view at one angle of the rotation.
Figure 6:
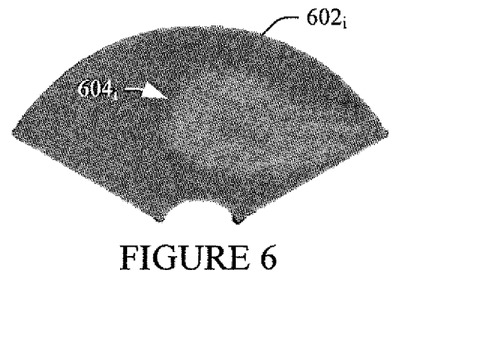
FIG. 6 illustrates a sagittal image.
Figure 7:
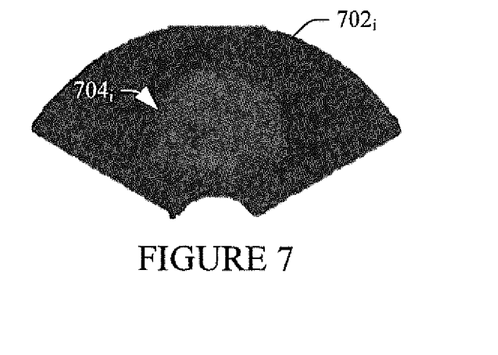
FIG. 7 illustrates a transverse image.

FIG. 5 shows a sagittal FOV $212_i$ and a transverse FOV $218_i$, where i is an index, at a particular angle along the arc 402 in connection with an object 502 (e.g., an anatomical organ such as a prostate). FIG. 6 shows a sagittal image $602_i$ for the sagittal FOV $212_i$ and includes a sagittal slice $604_i$ of the object 502, and FIG. 7 shows a transverse image $702_i$ for the transverse 218$_i$ and includes a transverse slice $704_i$ of the object 502. In FIGS. 4-7, the sagittal FOVs 212 lies in a z-y plane and the transverse FOVs 218 lies in an x-y plane of a Cartesian coordinate system.

For data acquisition, the user first rotates the probe 104 in one direction until the image for the transverse FOV does not include any of the objects 502. This marks the beginning of the arc 402. The user then user rotates the probe 104 in the opposite direction and through the arc 402, acquiring data with both the sagittal and the transverse arrays 208 and 214, and finishing when an image for the transverse FOV that does not include any of the object 502. This marks the ending of the arc 402. This assumes no intentional translational movement.

To estimate the translational and rotation movement of the probe, the data analyzer 124 estimates a degree of rotation and translation from one frame to a next frame (i.e. frame-to-frame). In one instance, the parameters estimated for this are those of an affine transform, which, generally, is a function between affine spaces which preserves points, straight lines and/or planes through translation, rotation, and/or stretching. An example of an affine transform matrix describing a change from frame k to frame k+1 is the following:

$$\begin{bmatrix} \cos(t) & \sin(t) & bx \\ -\sin(t) & \cos(t) & by \\ 0 & 0 & 1 \end{bmatrix}.$$

To place samples from the frame k+1 relative to samples from the frame k in 3-D space, all samples from the frame k+1 are translated by an amount (x,y)=(bx, by) in the x-y plane, where the x-y plane is the plane of the primary tracking image, and rotated by "t" radians in the x-y plane. Correspondingly, the motion of the probe in the y-z-plane, voluntary or not, may be estimated from the images of the imaging array, i.e. the array that is used for building the 3-D volume. In one instance, only the displacement, bz, in the z-direction is estimated. In another instance, another affine transform matrix, constrained by a given displacement in the y-direction, may be estimated:

$$\begin{bmatrix} 0 & 0 & 1 \\ -\sin(v) & \cos(v) & by \\ \cos(v) & \sin(v) & bz \end{bmatrix}.$$

To place samples from the corrected frame k+1 relative to samples from the frame k in 3-D space, all samples from the corrected frame k+1 are translated by an amount (y,z)=(0, bz) in the y-z plane and rotated by "v" radians in the y-z plane.

In another instance of data acquisition, the user may choose to push or pull-back of the transducer as the primary motion of the transducer. In that case, the images of the transverse array are used for building the volume, and the sagittal array is the primary tracking array. Also in this instance, a 3-D volume may be built by estimating the parameters by two affine transforms.

In another instance of data acquisition, the organ may be too large to be covered by a single sweep causing the user to perform two or more overlapping sweeps of the organ. In this case, a number of partly overlapping volumes are created. For data processing and visualization, the overlapping volumes are combined to a single volume. In one instance, the partly overlapping volumes are resampled to a common, regular 3-D sampling grid. This can be done in three parts. In the first part, each of the partial 3-D volumes is resampled to a regular sampling grid using interpolation of samples from the nearest frames. Each of these partial volumes are defined by the location and orientation of the first frame in the partial volume. In the second part, one of the regular 3-D sampling grids is selected as the common reference. Furthermore, the displacement and rotation of each of the other regular sampling grids to the common reference is estimated. In the third part, the data from the original frames are resampled to the common, regular sampling grid using interpolation.

The number of frames to make the 3-D image depends on the 3-D algorithm. For synthetic aperture beamforming, a maximum rotational speed determines the number of frames. If only the volume of the object of interest is being computed, then fewer frames are required. With other algorithms, the rotational speed is determined by the user. Generally, for a five to twelve second (5-12 s) scan at approximately twenty frames per second (25 fps), the images will have about three hundred and seventy-two (372) lines.

The data analyzer 124 determines a rotational speed and compares it with a predetermined maximum rotational speed range. For synthetic aperture imaging, the maximum rotational speed is set by half the beam-width at a narrowest point of the beam from the imaging plane, measured in the transverse direction. The data analyzer 124, as briefly discussed above, can visually present the results, which may include the rotational speed is too slow or too fast, or within the predetermined range. As discussed herein, this can be through text, numbers, color, graphical indicia, etc.

Figure 8:
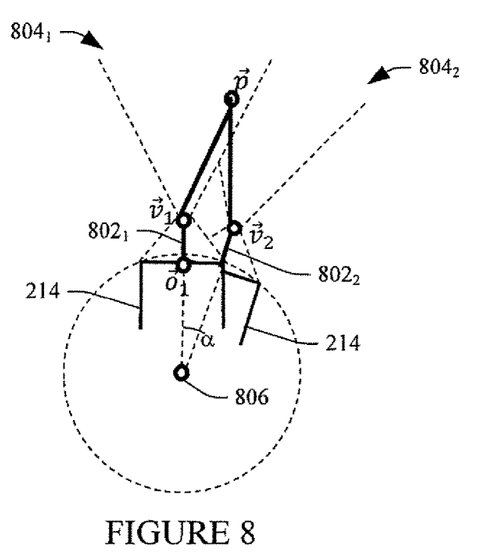
FIGS. 8 and 9 provide a non-limiting example for determining a data point for a 3-D image using a synthetic aperture algorithm.
Figure 9:
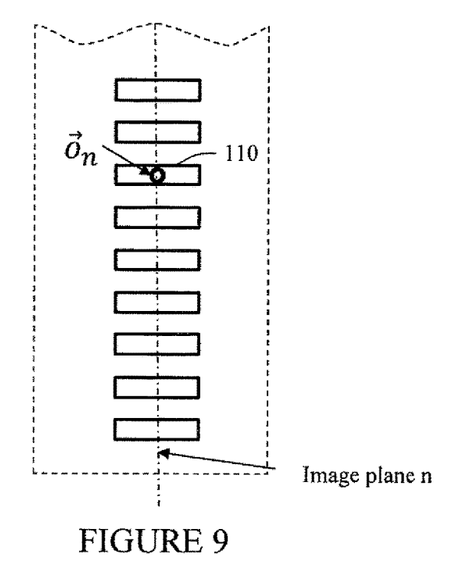

FIGS. 8 and 9 provide a non-limiting example for determining a data point for a 3-D image using a synthetic aperture algorithm.

FIG. 8 shows a line 802$_1$ for a plane 804$_1$ and a line 802$_2$ for a plane 804$_2$. The line 802$_2$ is angularly displaced from the line 802$_1$ by an angle α, with respect to an axis of rotation 806, and hence the lines 802$_1$ and 804$_1$ are at different angles of rotation of the probe 104. The lines 802$_1$ and 804$_1$ have a same position relative to the array 214, which is rotated. The beams have a fixed focus in the transverse direction, which is the direction of rotation, and the focus is determined by a focusing lens. The electrical signals from the two lines 802$_1$ and 804$_1$ are beamformed, which creates new lines, which have dynamic focusing in the transverse plane.

In these figures, $\vec{o}_1$ represents a center of an element 110 in a plane n=1 (FIG. 8), and $\vec{o}_n$ represents a center of the element 110 in a plane n (FIG. 9). The line 802$_1$ is formed in the plane n=1 and is perpendicular to the element 110, and the line 802$_2$ is formed in the plane n=2, which is angularly displaced from the plane n=1 by the angle α, and is perpendicular to the element 110. $\vec{v}_1$ and $\vec{v}_2$ represent virtual sources (fixed focus in elevation) for the planes n=1 and n=2. $\vec{p}$ represents a point in the scanned volume, where the beam is focused in the elevation direction.

A signal at any point can be determined as shown in EQUATION 1:

$$s(\vec{p}) = \sum_{n \in N(\vec{p})} y_n \left( \frac{2(|\vec{v}_n - \vec{o}_n| + |\vec{p} - \vec{v}_n|)}{c} \right), \quad \text{EQUATION 1}$$

where $s(\vec{p})$ represents the signal, $N(\vec{p})$ represents a set of planes that span the point $\vec{p}$, $y_n$ represents beamformed RF lines, $\vec{v}_n$ represents a virtual source in a plane n, $\vec{o}_n$ represents a center of an element in the plane n, and c represents the speed of sound. In other words, the signal $s(\vec{p})$ at a point $\vec{p}$ is a summation of all samples from the beamformed RF lines $y_n(t)$ for those planes n whose extent in elevation direction spans the point $\vec{p}$. The time instances t are calculated as the propagation time from an origin of the beam $\vec{o}_n$ through the virtual source $\vec{v}_n$ to the point of interest $\vec{p}$ and back to the element 110.

Figure 10:
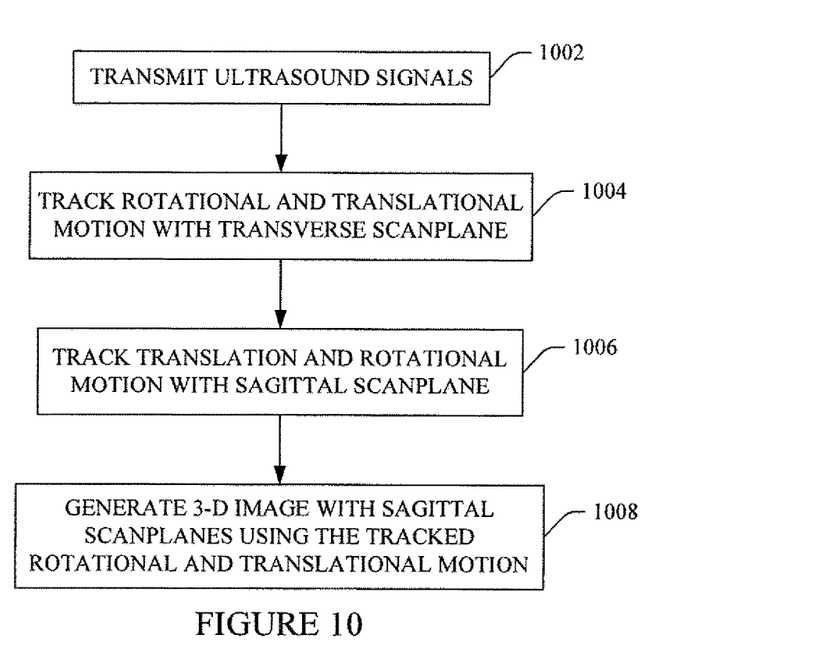
FIG. 10 illustrates an example method in accordance with an embodiment(s) herein.

FIG. 10 illustrates a method in accordance with an embodiment described herein.

It is to be appreciated that the order of the following acts is provided for explanatory purposes and is not limiting. As such, one or more of the following acts may occur in a different order. Furthermore, one or more of the following acts may be omitted and/or one or more additional acts may be added.

At 1002, ultrasound signals are transmitted from two arrays of a biplane transducer array during a scan in which the probe is manually rotated during data acquisition.

At 1004, a transverse scanplane from the transverse array is employed to track rotational motion of the probe and unintentional translational motion of the probe, as described herein and/or otherwise.

At 1006, a sagittal scanplane from the sagittal array employed to track translational motion of the probe and unintentional rotational motion of the probe, as described herein and/or otherwise.

At 1008, a 3-D image is generated with the sagittal scanplanes using both the tracked rotational and translational motion, as described herein and/or otherwise.

The approach described herein allows for an accurate 3-D ultrasound volume to be constructed using only free-hand scanning. Below describes several non-limiting applications of the approach described.

In one instance, the biplane transducer is used where one array is used for alignment/registration and the other array for the data acquisition of the 3-D image. The alignment array performs in-plane motion until the entire organ of interest is captured by the other array. The data from neighboring frames from the alignment array are co-registered, providing a change of orientation of the imaging array from frame to frame in 3-D space. For example, the data from neighboring frames are fit together using the estimates of translation and rotation. The 3D image is constructed by scanconverting the data from the array that does not perform the in-plane motion. Panoramic imaging allows on-the-fly accurate measurements of the translation and rotation and a measure of fidelity of the registration to ensure that out of plane motion is detected and flagged to the user, improving the acquisition of data and/or providing a fidelity measure for the entire 3-D reconstruction.

In another instance, data from both transducer arrays are used for registration. This is useful for capturing data of an object that is too large to be visualized in full during a single sweep, e.g. a prostate enlarged due to benign prostatic hyperplasia (BPH). The transducer motion in this case may be a combination of slowly pulling the transducer while rotating it back and forth. In this case, panoramic imaging is applied in both imaging planes to robustly reveal the motion of the arrays.

In another instance, the acquired volume is used for accurate registration to volumetric data from other modalities such as magnetic resonance imaging (MRI), e.g., for ultrasound guided biopsies. The volume may also be overlaid with pseudo-data such as the expected path for a biopsy needle.

In another instance, the acquired volume is used to automatically segment an accurate prostate volume, which is a challenge in ultrasound, not only because the measurements today are based on two still images and an assumption that the prostate is an ellipsoid but also because these images often fail to visualize the entire prostate for patients with BPH making today's measurements very inaccurate for the most interesting group of patients.

In another instance, the approach described herein is used for displaying in real-time and/or during cine play the relation of the current frame to a 3-D model, including the scanning object so that the orientation of the current ultrasound image to the scanning object may be immediately understood by a user or an external reviewer of the exam. The 3D-model may be sliced in standard anatomical views providing lower fidelity images but ones that may be readily compared with standard view MRI data or data from an atlas. The information can be stored along with the image data, so that a rendition of the 3D-model can change corresponding to the way the users select a particular frame in the cine buffer.

In another instance, the approach described herein is implemented with ultrasound probe E14C4t, E10C4 and/or E14CL4b for automatic prostate volume measurement. This includes visual cues to the operator, tracking of the motion, segmentation, and automatic volume measurement.

In another instance, the approach described herein is used to create 3-D volumes of not only B-mode data and flow data, but also 3D measurements of stiffness using free hand elastography or shear-wave/acoustic radiation force imaging, using the approach described herein to create 3D maps of stiffness.

For example, the approach described herein can be used with shear wave elasticity imaging (SWEI), which uses acoustic radiation force of focused ultrasound to create shear waves in soft tissue to map tissue elasticity. The shear wave speed is determined by the shear modulus of tissue, which is highly sensitive to physiological and pathological structural changes of tissue. The variation of the shear wave speed increases in many tissues in the presence of disease, e.g. the cancerous tissues can be significantly stiffer than normal tissue. Example workflow includes: scan plane with SWEI, prompt the user to move the transducer, track the motion, and acquire a new plane.

In another example, the approach described herein can be used with acoustic radiation force impulse (ARFI) imaging, which uses acoustic radiation force to generate images of the mechanical properties of soft tissue. With increasing acoustic frequencies, the tissue does not respond fast enough to the transitions between positive and negative pressures, and energy is deposited into the tissue, which in a momentum transfer that generates a force that causes displacement of the tissue. This displacement is detected and used to derive additional information. Example workflow includes: scan plane with SWEI, prompt the user to move the transducer, track the motion, and acquire a new plane.

In another instance, the approach described herein can be used for general 3D volume imaging for the purpose of reexamination, follow-up and/or monitoring, and/or fusion, which can replace current systems that use electromagnetic or optical tracking of the transducer position. This can be achieved through active tracking of motion in one or more planes.

In another instance, the approach described herein can be used for targeted biopsies. Example workflow includes: acquire 3-D volume with SWEI and/or Color, move the transducer freely and track the position using motion estimation from the two planes, register a current real-time image with the 3-D volume, and, when a suitable position is reached, perform the biopsy.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:
1. An ultrasound imaging system, comprising:
a biplane ultrasound probe, including:
  a sagittal array; and
  a transverse array; and
a console, including:
  a transmit circuit configured to control the sagittal and transverse arrays to emit ultrasound signals to a structure while the biplane ultrasound probe is at least one of manually rotated and manually translated;
  a receive circuit configured to receive electrical signal produced by the sagittal and transverse arrays in response to the sagittal and transverse arrays receiving echoes produced in response to the corresponding ultrasound signals interreacting with the structure; and
  wherein the console is configured to construct a three-dimensional image with the electrical signals from one of the sagittal array or the transverse array and a transformation matrix

$$\begin{bmatrix} \cos(t) & \sin(t) & bx \\ -\sin(t) & \cos(t) & by \\ 0 & 0 & 1 \end{bmatrix},$$

where x and y are coordinates in an x-y plane, t represents a rotation in the x-y plane, and b represents a translation in the x-y plane.

2. The imaging system of claim 1, wherein the console is further configured to determine a manual translational motion of the biplane ultrasound probe from the electrical signals from the sagittal array, wherein the console constructs the three-dimensional image with the determined manual translational motion.

3. The imaging system of claim 1, wherein the console is further configured to determine a manual translation motion of the biplane ultrasound probe from the electrical signals from the sagittal array for the transformation matrix and a manual rotational motion of the biplane ultrasound probe from the electrical signals from the transverse array for the transformation matrix.

4. The imaging system of claim 1, further comprising:
a beamformer configured to beamform the electrical signals using a synthetic aperture algorithm to generate data for the three-dimensional image, wherein the console constructs the three-dimensional image with the generated data.

5. The imaging system of claim 1, wherein the console is further configured to determine a manual rotational motion of the biplane ultrasound probe from the electrical signals from the transverse array, wherein the console constructs the three-dimensional image with the determined manual rotational motion.

6. The imaging system of claim 5, further comprising:
a beamformer configured to beamform individual sagittal and transverse scanplanes from the electrical signals from both the sagittal and transverse arrays.

7. The imaging system of claim 6, wherein the console is further configured to determine a manual translational motion of the biplane ultrasound probe, wherein the console constructs the three-dimensional image by spatially aligning the sagittal scanplanes with the manual translation and rotational motion.

8. The imaging system of claim 1, wherein the transformation matrix estimates a degree of rotation and translation from frame-to-frame.

9. The imaging system of claim 8, wherein the transformation matrix includes an affine transform that translates and rotates samples from a first frame to align the first frame with a next frame.

10. The imaging system of claim 1, wherein the console is further configured to determine a rotational speed of the biplane ultrasound probe, compare the determined rotational speed with a predetermined rotational speed range, and display a result of the comparison.

11. The imaging system of claim 10, wherein the result indicates the rotational speed is faster than the predetermined rotational speed range.

12. The imaging system of claim 10, wherein the result indicates the rotational speed is slower than the predetermined rotational speed range.

13. The imaging system of claim 10, wherein the result indicates the rotational speed is within the predetermined rotational speed range.

14. The imaging system of claim 10, wherein the predetermined rotational speed range is set by half a beam-width at a narrowest point of beam from an imaging plane, measured in a transverse direction.

15. A console of an ultrasound imaging system, comprising:
a transmit circuit configured to control a sagittal array and a transverse array of a biplane probe to emit ultrasound signals to a structure while the biplane probe is manually rotated and translated;
a receive circuit configured to receive electrical signal produced by the sagittal and transverse arrays in response to the sagittal and transverse arrays receiving echoes produced in response to the corresponding ultrasound signals interreacting with the structure; and
wherein the console is configured to construct a three-dimensional image with a transformation matrix $$\begin{bmatrix} 0 & 0 & 1 \\ -\sin(v) & \cos(v) & by \\ \cos(v) & \sin(v) & bz \end{bmatrix},$$

where y and z are coordinates in y-z plane, v represents a rotation in the y-z plane and b represents a translation in the y-z plane, and the electrical signals from the sagittal or transverse array.

16. The console of claim 15, wherein the three-dimensional image is constructed by scan converting data from one of the sagittal array or the transverse array.

17. The console of claim 15, wherein data from both the sagittal array and the transverse array is used for registration.

18. The console of claim 15, wherein data from neighboring frames from one of the sagittal array or the transverse array are co-registered, providing a change of orientation of the other of the one of the sagittal array or the transverse array from frame to frame in 3-D space.

19. The console of claim 18, wherein the data from the neighboring frames are fit together using an estimation of degree of translation and rotation.

20. The console of claim 15, wherein a number of partly overlapping volumes are created and overlapping volumes are combined into a single volume.

21. The console of claim 20, wherein each of the partly overlapping volumes is resampled to a regular sampling grid using interpolation of samples from nearest frames to create plurality of regular sampling grids, one of the regular sampling grids is selected as a common reference, and data from original frames are resampled to a common, regular 3-D sampling grid using interpolation.

* * * * *